United States Patent
Rejndrup

(10) Patent No.: US 12,148,510 B2
(45) Date of Patent: *Nov. 19, 2024

(54) SYSTEMS AND METHODS FOR AUTOMATED EDIT CHECK GENERATION IN CLINICAL TRIAL DATASETS

(71) Applicant: Omnicomm Systems, Inc., Fort Lauderdale, FL (US)

(72) Inventor: Kim Rejndrup, Fort Lauderdale, FL (US)

(73) Assignee: OMNICOMM SYSTEMS, INC., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/126,199

(22) Filed: Mar. 24, 2023

(65) Prior Publication Data

US 2024/0062855 A1 Feb. 22, 2024

Related U.S. Application Data

(63) Continuation of application No. 16/866,455, filed on May 4, 2020, now Pat. No. 11,615,868, which is a continuation-in-part of application No. 16/549,547, filed on Aug. 23, 2019, now abandoned.

(51) Int. Cl.
| | |
|---|---|
| G16H 10/20 | (2018.01) |
| G06F 40/186 | (2020.01) |
| G16H 10/60 | (2018.01) |
| G16H 15/00 | (2018.01) |

(52) U.S. Cl.
CPC ........... *G16H 10/20* (2018.01); *G06F 40/186* (2020.01); *G16H 10/60* (2018.01); *G16H 15/00* (2018.01)

(58) Field of Classification Search
None
See application file for complete search history.

(56) References Cited

U.S. PATENT DOCUMENTS

| | | | | |
|---|---|---|---|---|
| 2002/0049624 | A1* | 4/2002 | Raveis, Jr. | G06Q 40/03 705/38 |
| 2006/0167905 | A1* | 7/2006 | Liu | G06F 40/226 |
| 2007/0288903 | A1* | 12/2007 | Manglik | G06F 8/60 717/124 |
| 2008/0021737 | A1* | 1/2008 | Dutt | G16H 10/20 705/2 |
| 2009/0083703 | A1* | 3/2009 | Grady | G06Q 10/10 717/109 |
| 2009/0150447 | A1* | 6/2009 | Anderson | G06F 16/217 |
| 2011/0302003 | A1* | 12/2011 | Shirish | G06Q 10/0639 705/7.38 |
| 2015/0286802 | A1* | 10/2015 | Kansara | G16H 10/20 705/3 |
| 2018/0046609 | A1* | 2/2018 | Agarwal | G06F 3/0482 |
| 2020/0254407 | A1* | 8/2020 | Wilson | B01F 33/8442 |
| 2020/0279623 | A1* | 9/2020 | Ozeran | G06F 16/215 |
| 2020/0395103 | A1* | 12/2020 | Ramakrishnan | G06F 16/31 |
| 2021/0057052 | A1* | 2/2021 | Rejndrup | G16H 10/20 |

* cited by examiner

*Primary Examiner* — Howard Cortes
(74) *Attorney, Agent, or Firm* — Snell & Wilmer L.L.P.

(57) ABSTRACT

A system for automated edit check generation is disclosed. The system may write a template edit check based on a custom edit check, add a parameter set for the template edit check, add a value for each parameter of the parameter set, and generate an edit check based on the template edit check, the parameter set, and the value.

15 Claims, 10 Drawing Sheets

Form Visit Association

| Forms/Visits | Log Forms | Screening | Day 0 | Day 14 | Day 28 | Day 56 | Day 84 | Day 124 | Day 136 | Day 146 | Follow-up |
|---|---|---|---|---|---|---|---|---|---|---|---|
| Demographics | | X | | | | | | | | | |
| Inclusion/Exclusion | | X | | | | | | | | | |
| Medical History | | X | | | | | | | | | |
| Pain Assessment (Likert Scale) | | X | X | X | X | X | X | X | X | X | |
| Vital Signs | | | X | X | X | X | X | X | X | X | |
| Exposure | X | | X | X | X | X | X | X | X | X | |
| Chemistry | X | X | X | X | X | X | X | X | X | X | |
| Adverse Events | | | | | | | | | | | |
| Con Meds | | | | | | | | | | | |
| Termination | | | | | | | | | | | X |

SYSTEMS AND METHODS FOR AUTOMATED EDIT CHECK GENERATION IN CLINICAL TRIAL DATASETS

CROSS REFERENCE TO RELATED APPLICATIONS

This application is a continuation of U.S. patent application Ser. No. 16/549,547, filed on Aug. 23, 2019 and entitled "SYSTEMS AND METHODS FOR AUTOMATED EDIT CHECK GENERATION IN CLINICAL TRIAL DATASETS," which is a continuation in part of, and claims priority to, and benefit of U.S. patent application Ser. No. 16/549,547, filed on Aug. 23, 2019 and entitled "METHOD FOR ELECTRONICALLY GENERATING EDIT CHECKS FROM A REFERENCE EDIT CHECK FOR USE IN DATA CAPTURING SOFTWARE" which is incorporated by reference herein in its entirety.

FIELD

This disclosure generally relates to big data systems and, more particularly, to data capturing and validations systems for clinical trials.

BACKGROUND

Data generated in a clinical trial of pharmaceuticals, medical devices, and/or the like are defined by the study protocol and, in particular, the goal of the investigative trial. Study protocols are therefore highly depending on the specific goals of the researcher and, in this regard, are highly custom. Traditional software systems for capturing data in clinical trials include data entry via one or more forms capturing the required data. In conjunction with these forms, the study designer often needs to specify rules. As a non-limiting example, if a form is capturing blood pressure (BP), then the study designer specifies a rule (i.e. writing code for the software) which would raise a query (error) if the systolic BP is lower than the diastolic BP. In this regard, the system may prompt the researcher to gather and enter further data into the system. The written code for these rules can be referred to as "edit checks." Given the nature of study protocols, traditional data capturing software and the related edit checks are also highly custom and therefore unsuited to multiple studies and/or differing investigations.

SUMMARY

A system, method, and computer readable medium (collectively, the "system") is disclosed for automated edit check generation. In various embodiments, the system may write a template edit check based on a custom edit check, add a parameter set for the template edit check, add a value for each parameter of the parameter set, and generate an edit check based on the template edit check, the parameter set, and the value.

In various embodiments, the system may test the edit check. In various embodiments, the system may identify the custom edit check, wherein the identifying is performed prior to writing the template edit check. In various embodiments, the system may determine a depth for each parameter of the parameter set. In various embodiments, the system may generate a dynamic code for each depth of the parameter set, wherein the dynamic code is configured to replace variables of the depth and generate the edit check.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION

The subject matter of the present disclosure is particularly pointed out and distinctly claimed in the concluding portion of the specification. However, a more complete understanding of the present disclosure may be obtained by referring to the detailed description and claims when considered in connection with the drawing figures, wherein like numerals denote like elements.

FIG. 3 is a block diagram illustrating a visit set data structure in a system for automated edit check generation, in accordance with various embodiments;

FIG. 7 illustrates a template construction interface in a system for automated edit check generation, in accordance with various embodiments;

FIG. 8 illustrates a template validation interface in a system for automated edit check generation, in accordance with various embodiments;

FIG. 9 illustrates a variables data editing interface in a system for automated edit check generation, in accordance with various embodiments.

DETAILED DESCRIPTION

Figure 1:
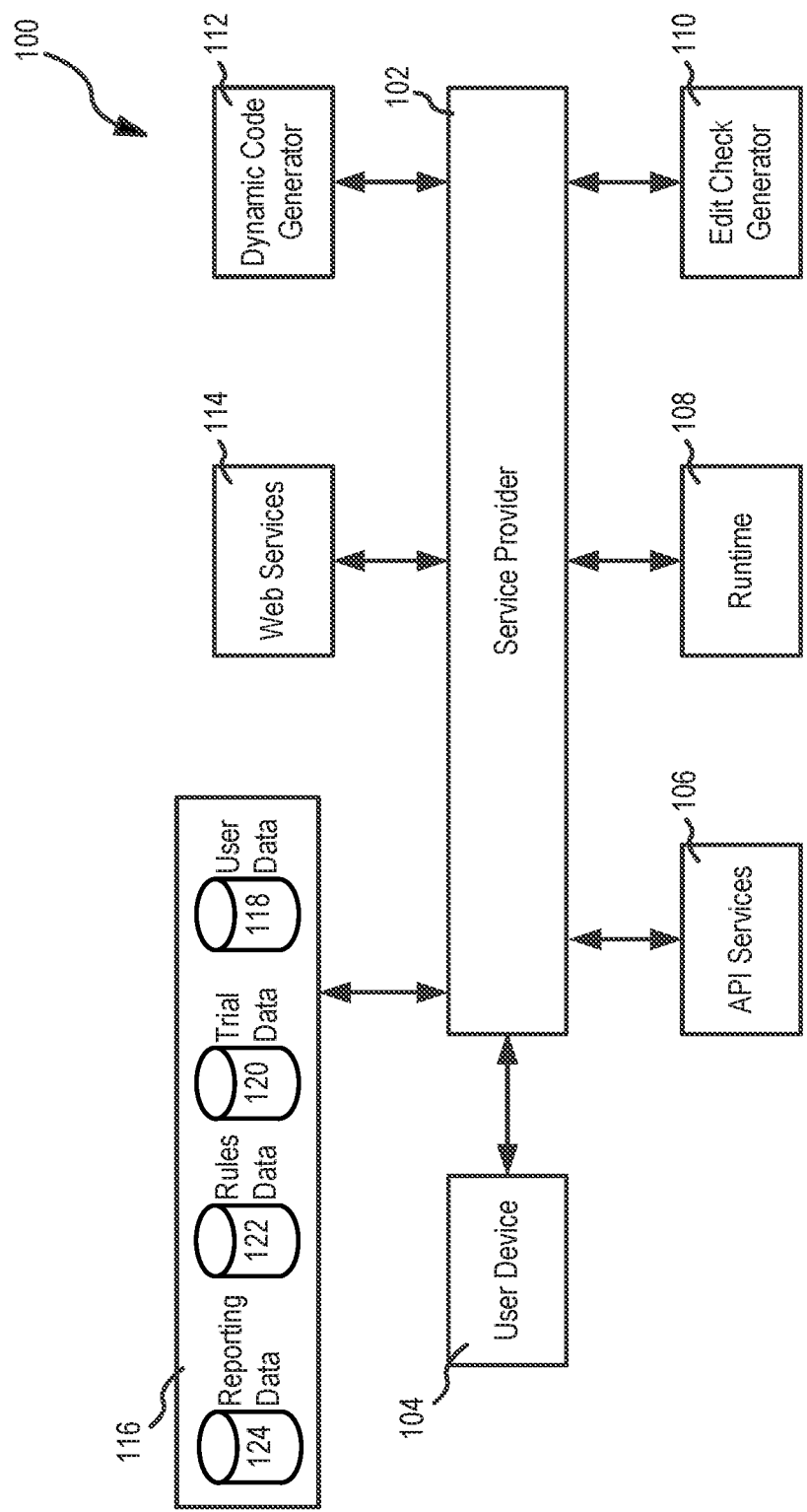
FIG. 1 is a block diagram illustrating a system for automated edit check generation, in accordance with various embodiments.

The detailed description of various embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Furthermore, any reference to singular includes plural embodiments, and any reference to more than one component may include a singular embodiment.

The system may provide a greater level of sophistication and/or control for clinical data capture systems. For example, traditional data capture systems may be highly custom, semi-automated, and/or manual processes. In this regard, customization of traditional data capture systems, and/or the like based on study specific procedures and/or variables may tend to be time consuming or inefficient with regard to computational resources. While prior art systems implement custom architecture and typically demand one-off edit checks, the current system may incorporate customizable forms enabling edit checks to be generated on demand and tailored to individual study requirements. For example, edit checks may be generated based on edit check metadata collected by the system from custom coded edit checks or based on an associate between a defined parameter set and associated values which may be tailored to the particular study rules.

As such, the system may tend to reduce custom coding along with enabling enhanced automation features. In this regard, the system may also reduce the cost of development or system processing time for edit checks, reduce network utilization, and/or reduce data storage overhead. The system may increase data reliability or accuracy by enabling standardization of edit check forms and data capture. The system may also reduce a redundant code base, thereby reducing a demand for system resources. The system may simplify data mining and enhance user experience by enabling immediate generation of edit checks. Benefits of the present disclosure may apply to any suitable data capture environment benefiting of periodic updates or rules based follow up. For example, the present disclosure may apply in non-clinical contexts such as financial reporting contexts, payment contexts, academic contexts, as well as clinical contexts including primary care, medical services, medical research, and/or the like.

This process improves the functioning of the computer. For example, standardizing edit check generation increases processing efficiency. Similarly, the process increases the reliability and speed of data presentation by enabling metadata capture and error correction via automated edit check generation. In various embodiments, a rules based process model is enabled that increases the reliability and speed edit check generation. Users may select from standard rules sets and configurable variables, i.e. rules metadata to generate the edit checks. In this regard, by transmitting, storing, and/or accessing data using the processes described herein, the quality of the captured data is improved and errors are reduced. Such improvements also increase the efficiency of the network by accelerating data capture, reducing the portion of duplicated inputs, and reducing redundant data requests. In various embodiments, generating edit checks based on standardized rules sets significantly reduce back end processing and reduce troubleshooting for component processes. In various embodiments, the processes may increase network availability by reducing front end and back end process calls. In this regard, the processes may save processing resources including CPU time, memory resources, and/or network resources. For example, in a study comprising 5,000 edit checks the system may automatically generate between 20% and 50% of the edit checks tending thereby to save storage space, reduce compilation time, and to improve data quality.

As used herein, "electronic communication" means communication of at least a portion of the electronic signals with physical coupling (e.g., "electrical communication" or "electrically coupled") and/or without physical coupling and via an electromagnetic field (e.g., "inductive communication" or "inductively coupled" or "inductive coupling"). As used herein, "transmit" may include sending at least a portion of the electronic data from one system component to another (e.g., over a network connection). Additionally, as used herein, "data," "information," or the like may include encompassing information such as commands, queries, files, messages, data for storage, and the like in digital or any other form.

As used herein, "satisfy," "meet," "match," "associated with", or similar phrases may include an identical match, a partial match, meeting certain criteria, matching a subset of data, a correlation, satisfying certain criteria, a correspondence, an association, an algorithmic relationship, and/or the like. Similarly, as used herein, "authenticate" or similar terms may include an exact authentication, a partial authentication, authenticating a subset of data, a correspondence, satisfying certain criteria, an association, an algorithmic relationship, and/or the like.

Systems, methods, and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

With reference to FIG. 1, a system 100 for automated edit check generation is depicted according to various embodiments. System 100 may include various computing devices, software modules, networks, and data structures in communication with one another. System 100 may also contemplate uses in association with web services, utility computing, pervasive and individualized computing, security and identity solutions, autonomic computing, cloud computing, commodity computing, mobility and wireless solutions, open source, biometrics, grid computing and/or mesh computing.

In various embodiments, system 100 may comprise a service provider system 102 (i.e., service provider), a user device 104, an API services module 106, a runtime module 108, an edit check generator 110, a dynamic code generator 112, a web services module 114, and a database module 116 (i.e., a database). Any of these components may be outsourced and/or be in communication with service provider 102 via a network. System 100 may be computer based, and may comprise a processor, a tangible non-transitory computer-readable memory, and/or a network interface, along with other suitable system software and hardware components. Instructions stored on the tangible non-transitory memory may allow system 100 to perform various functions, as described herein. In various embodiments, service provider 102 may be configured as a central network element or hub to access various systems, engines, and components of system 100. Service provider 102 may comprise a network, computer-based system, and/or software components configured to provide an access point to various systems, engines, and components. Service provider 102 may be in operative and/or electronic communication with the user device 104, the API services module 106, the runtime module 108, the edit check generator 110, the dynamic code generator 112, the web services module 114, and the database module 116. In this regard, the service provider 102 may allow communication from user device 104 and database module 116 to systems, engines, and components of system 100.

In various embodiments, user device 104 may comprise software and/or hardware in communication with the service provider 102 via a network comprising hardware and/or software configured to allow a payment account owner, an administrator, a user, a customer, and/or the like, access service provider 102. User device 104 may comprise any suitable device that is configured to allow a user to communicate with a network and service provider 102. User device 104 may include, for example, a personal computer, personal digital assistant, cellular phone, kiosk, a mobile device, and/or the like and may allow a user to transmit voice communications and/or data.

In various embodiments, database module 116 may include any number of data structures or data elements such as user data 118, trial data 120, rules data 122, and reporting data 124. Database module 116 may be configured to maintain user data 118 such as, for example, data relating to a user such as, a user name, a device profile, a phone number, user configurations, user permissions, associated licenses and/or the like. Database module 116 may be configured to maintain trial data 120 such as, for example, trial specific forms, completed forms, patient data, study data, and/or the like. Database module 116 may be configured to maintain rules data 122 such as, for example, a template edit check, a parameter set, an edit check, validated edit checks, and/or the like. Database module 116 may be configured to maintain reporting data 124 such as, for example, metadata of the trial data 120 and/or the rules data 122, a date, a time, a process outcome data and/or status data, module status data, and/or the like.

In various embodiments, the API services module 106 may be configured to interface with third party applications and to enable structured addition, deletion, and/or modification of database 116 data. In various embodiments, the API services module 106 may be configured to pass commands from a network via the service provider 102 to the various systems, engines, and components of system 100. In this regard, the API services module 106 may provide a programmatic interface to the service provider 102 and the associated modules thereof. In like regard, the web services module 114 may be configured to provide an interface with various cloud based services (e.g., Infrastructure as a Service, Platform as a Service, etc.), network services, and/or the like such as, for example, MedDRA and WHODrug databases.

In various embodiments, the runtime module 108 may include a GUI interface to the various systems, modules, and engines of system 100. Runtime module 108 may be in operative and/or electronic communication with the user device 104, the API services module 106, the edit check generator 110, the dynamic code generator 112, the web services module 114, and the database module 116. In this regard, web services module 114 may allow communication from user device 104 to systems, engines, and components of system 100. In various embodiments, the runtime module may be configured to enable the user to conduct trials, build new trials, manage existing trials and related database data, and capture trial data.

In various embodiments, the edit check generator 110 may be configured to generate edit checks based on the rules data and the trial data. The edit check generator 110 may be configured to parse the trial data 120 and, based on the parsed trial data, generate the edit checks. In various embodiments, the dynamic code generator 112 may be configured to generate dynamic code based on the edit checks generated by the edit check generator 110.

Figure 2:
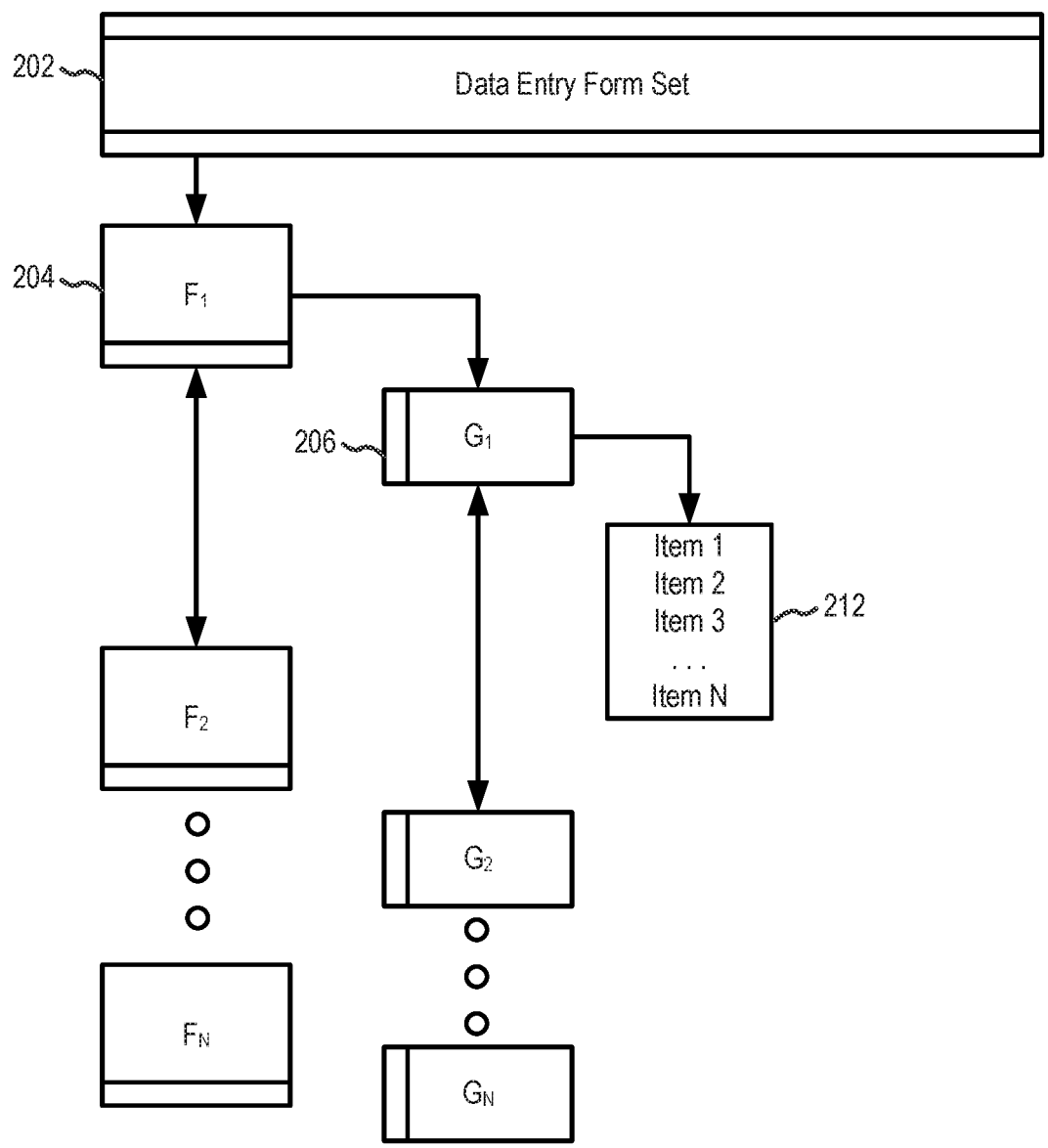
FIG. 2 is a block diagram illustrating a form set data structure in a system for automated edit check generation, in accordance with various embodiments.

In various embodiments and with reference to FIG. 2, a data structure 200 for form sets in system 100 is illustrated. Data structure 200 comprises a data entry form set 202 which may provide a basis for generation of edit checks by edit check generator 110. Form set 202 may include a plurality of forms 204, i.e., $F_1$, $F_2$, ... FN. Each form may comprise one or more groups 206, i.e. G1, G2, ... GN. Each group 206 may further comprise a plurality of items i.e., a first item, a second item, a third item ... an Nth item. In a study a form or form set may be repeated in multiple visits. That allows a user, an investigator, a researcher, and/or the like to track a research subject's data across visits and thereby develop a time based data set. For example, a patient's vitals may be tracked over time (e.g. weight loss, blood pressure, cholesterol, etc.).

In various embodiments, and with additional refence to FIG. 3, a data structure 300 for visit sets in system 100 is illustrated as a form-visit association table. In various embodiments, each form 202 of a form set may further be associated with a plurality of events 302 such, for example, visits (i.e., a visit event) defining an event array. For example, a "Demographics" form may be associated with a "Screening" event. In another example, each of a "Pain Assessment," "Vital Signs," "Exposure," and "Chemistry" form may be associated with a "day 0," "day 14," "day 28," "day 56," "day 84," "day 124," "day 136," and "day 146" visit event. In various embodiments, each visit event may be associated with a subject 304 such as, for example, a patient. A plurality of subjects may be associated with a higher order data structure such as, for example, a testing site. In various embodiments a plurality of the higher order structures may be combined to define a trial and may be stored in database module 116 as trial data 120. In various embodiments, "Log Forms" may be used to capture data which can occur at events outside of a normal visit. As a non-limiting example, an "Adverse Event" form may be generated by system 100 for events such as a headache which might occur while the patient is not under direct observation, whereas as vital signs, such as, weight, blood pressure etc. can be measured when the patient is under direct observation.

Figure 4:
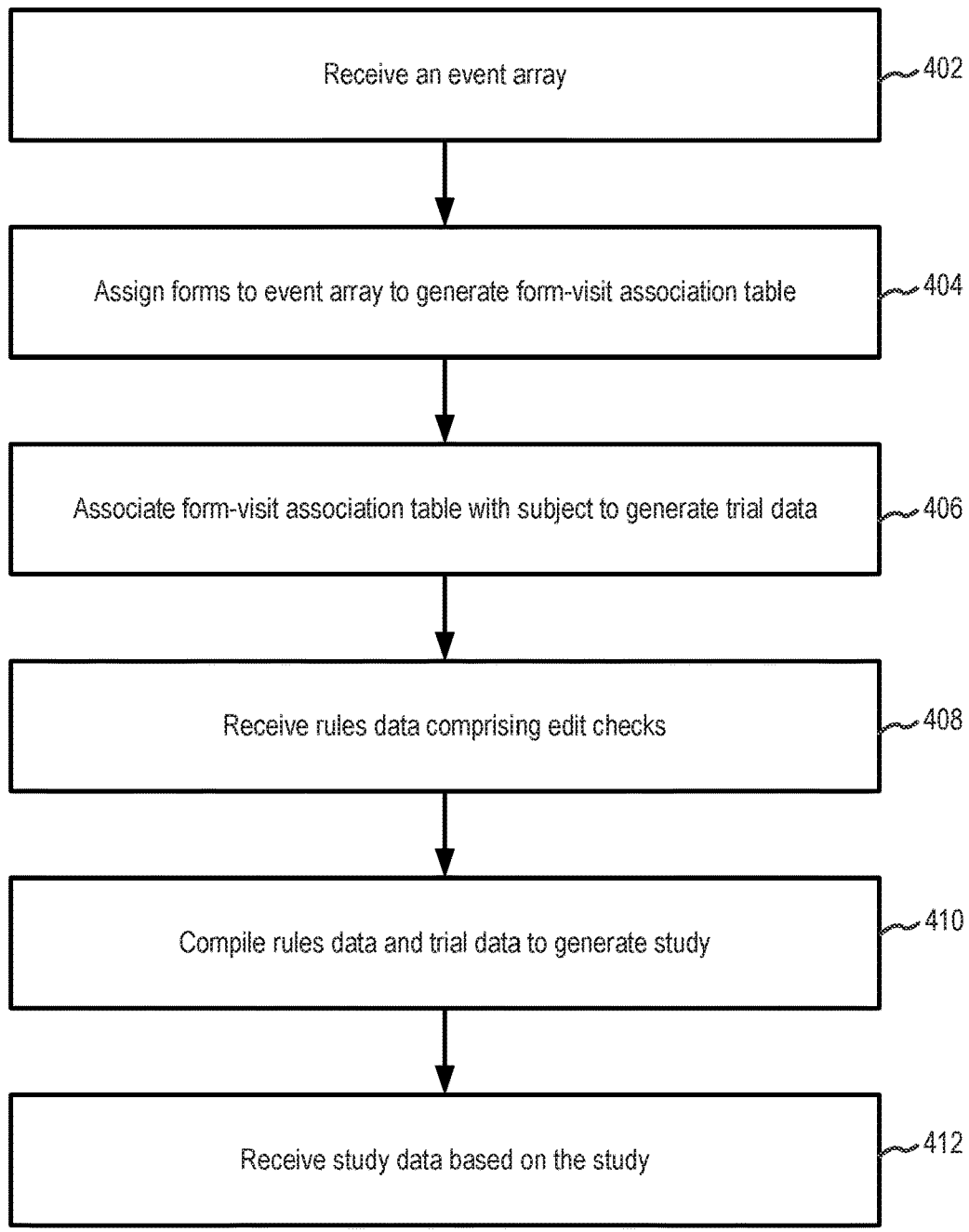
FIG. 4 illustrates a study generation process in a system for automated edit check generation, in accordance with various embodiments.
Figure 5:
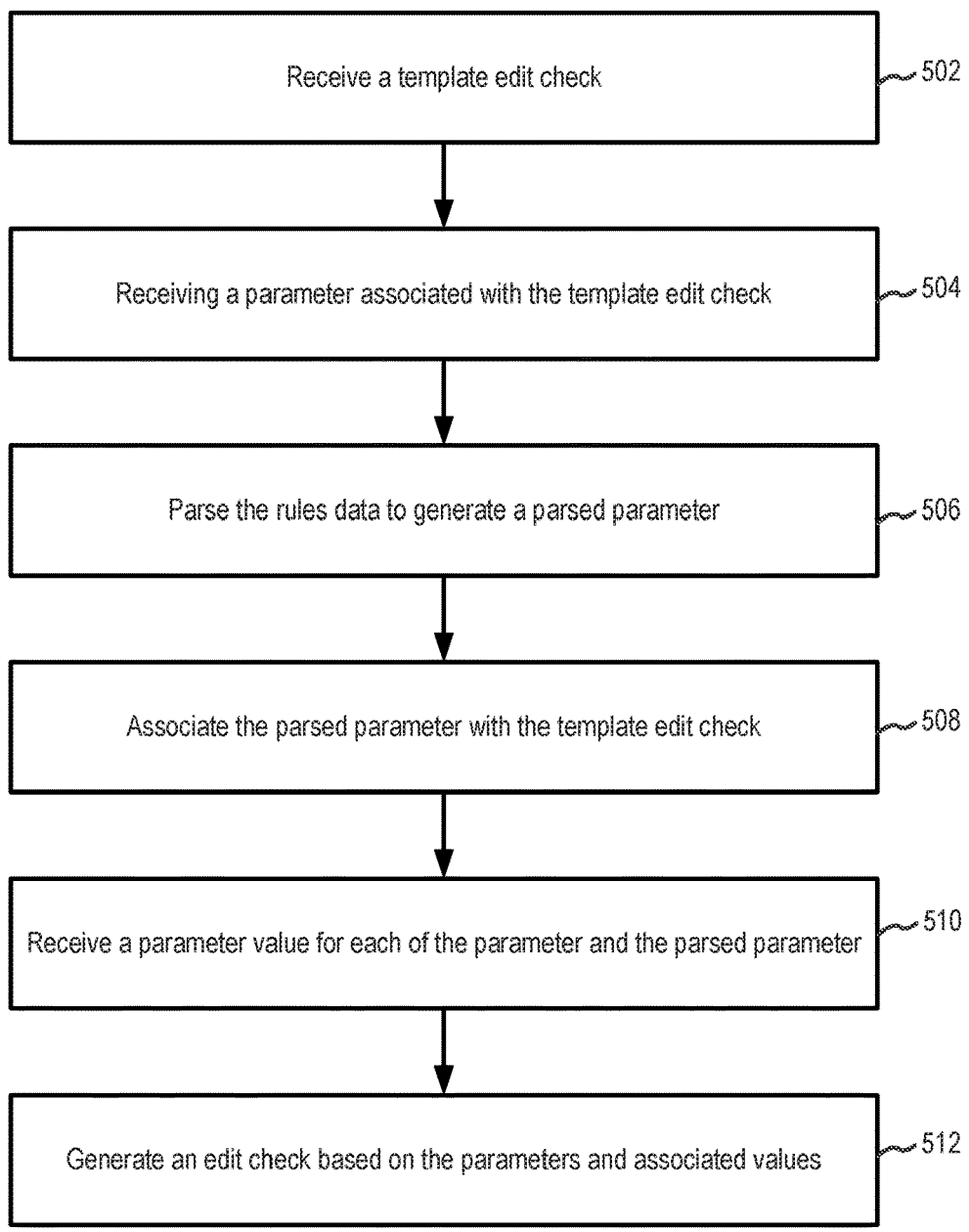
FIG. 5 illustrates an edit check generation process in a system for automated edit check generation, in accordance with various embodiments.
Figure 6:
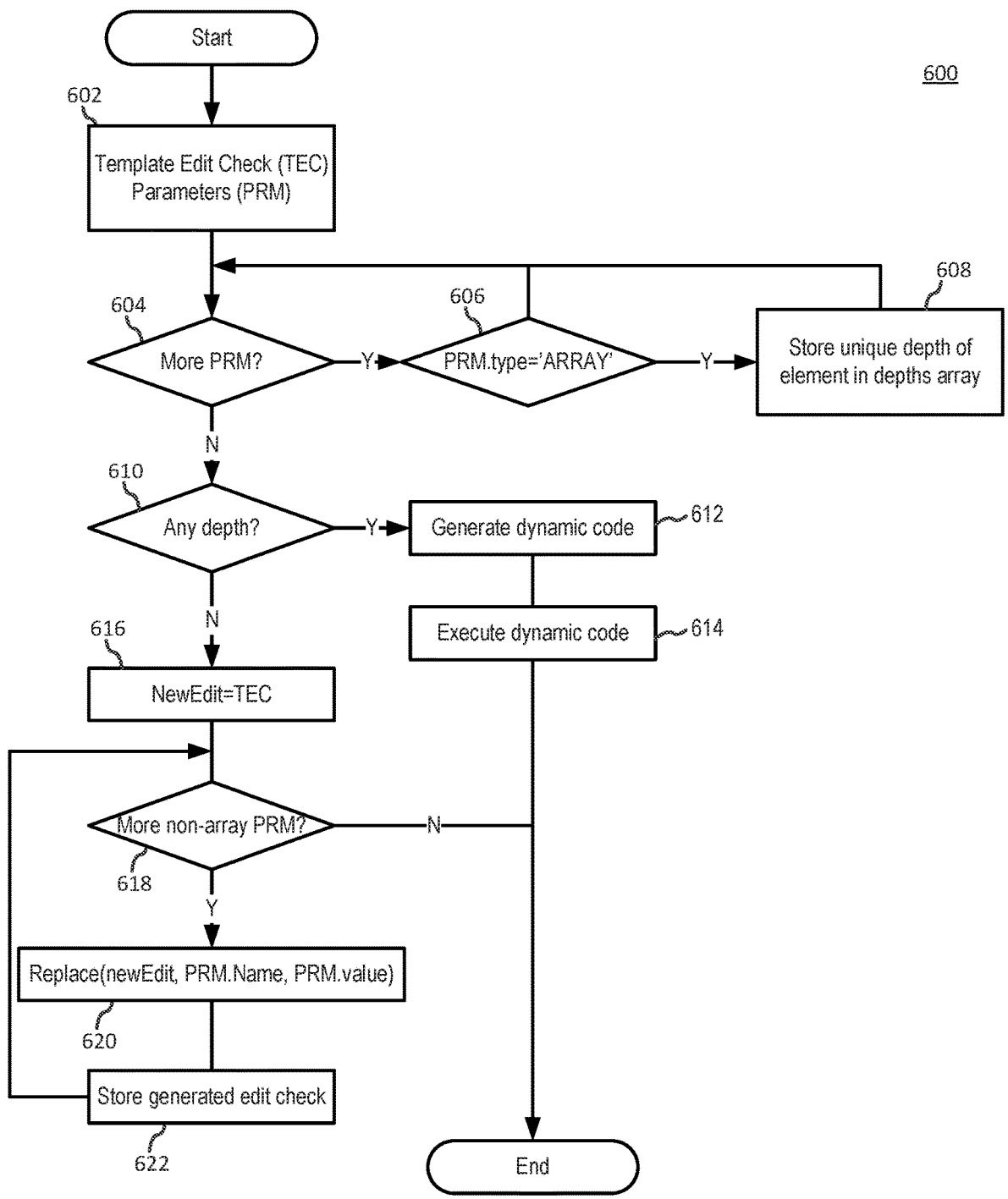
FIG. 6 illustrates an array depth handling process in a system for automated edit check generation, in accordance with various embodiments.

Referring now to FIGS. 4-6, the process flows depicted are merely embodiments and are not intended to limit the scope of the disclosure. For example, the steps recited in any of the method or process descriptions may be executed in any order and are not limited to the order presented. It will be appreciated that the following description makes appropriate references not only to the steps depicted in FIGS. 4-6, but also to the various system components as described above with reference to FIG. 1.

In various embodiments, and with reference to FIG. 4 a study generation process 400 of system 100 is illustrated. The system may receive an event array (step 402). For example, the system may receive an array of events 302. The system may assign forms to the event array to generate one or more form-visit association tables (step 404). For example forms 202 may be associated with the events 302 to generate one or more form sets defined by the form-visit associate table. In various embodiments, the system may associate a subject with the form-visit association table to generate trial data (step 406). For example, a plurality of subjects may be associated with a plurality of form-visit association tables and stored as trial data 120 of database module 116. The system may receive rules data comprising a plurality of custom edit checks (step 408). For example, the system may receive computer code which defines the edit checks and may store the edit checks as rules data 122 in database 116.

As an example, a custom edit check may be defined by the pseudo code below:

$$\left| \frac{[Patient].[Day\ 0].[VS].[VS1].[WEIGHT] - [Patient].[Day\ 14].[VS].[VS1].[WEIGHT]}{[Patient].[Day\ 0].[VS].[VS1].[WEIGHT]} \right| > 10\%$$

[Patient].[Day 0].[VS].[VS1].[WEIGHT] will at runtime return the weight (data value) for a specific patient on the "day 0" visit, on the "Vital sign" (VS) form, in the VS1 group. Where a user/study designer desires to calculate that the weight did not change more that 10% between visits for a patient, the user/study designer can write the edit check of paragraph [0037] for execution by system 100. The system may compile the rules data and the trial data to generate a study (step 410). For example, the rules data 122 may be associated with the trial data 120 to generate the study. The system may receive study data based on the study (step 412). In various embodiments, the system may associate the study data with the trial data 120.

In various embodiments, and with reference to FIG. 5 an edit check generation process 500 of system 100 is illustrated. The system may receive a template event check (step 502). In various embodiments, the template edit check may be based on the custom edit check and/or the rules data comprising the plurality of custom edit checks. In this regard, a custom edit check may serve as a reference (i.e., a reference edit check) for template generation. For example, a template edit check based on the edit check of paragraph [0037] may be defined by the pseudo code below:

$$\left| \frac{[Patient].[@VisitX].[VS].[VS1].[WEIGHT] - [Patient].[@VisitY].[VS].[VS1].[WEIGHT]}{[Patient].[@VisitX].[VS].[VS1].[WEIGHT]} \right| > @Ch$$

The template edit check may be configured to receive parameters so that the plurality of custom edit checks may be generated by edit check generator 110 based on the template edit check. The system may receive a parameter associated with the template edit check (step 504). In various embodiments, the parameter may comprise an array. For example, the template edit check of paragraph may define parameters @VisitX, @VisitY, and @Ch and may receive the array below:

| Parameter | Value |
|---|---|
| @VisitX | {Day 0, Day 14, Day 28, Day 56, Day 84, Day 124, Day 136} |
| @VisitY | {Day 14, Day 28, Day 56, Day 84, Day 124, Day 136, Day 146} |
| @Ch | 10% |

The system may parse the rules data to generate a parsed parameter (step 506). In various embodiments, the edit check generator 110 may query the database module 116 for rules data 122 associated with a study defined in the trial data 120. The edit check generator 110 may determine a relationship between classes of edit checks and parse the associated rules data to derive a parsed parameter. The system may associate the parsed parameter with the template edit check (step 508). In this regard, the edit check generator 110 may be configured to generate a template edit check comprising the parsed parameters associated with a set of related edit checks by populating the template with received parameters or parsed parameters. The system may receive a parameter value for each of the parameters and the parsed parameters (step 510). For example, @Ch may be a received parameter while @VisitX and @VisitY may be parsed parameters generated by edit check generator 110 and the system may receive the array values described in paragraph above. The system may generate a plurality of edit checks based on the parameters and associated values (step 512). For example, the edit check generator 110 may generate a number of edit checks corresponding to each of the array elements passed through the parameters.

In various embodiments and with additional reference to FIG. 6 an array depth handling process 600 in system 100 is illustrated. As seen the defined parameters and defined edit-check template are used by the system (e.g. edit check generator 110) to automatically generate edit checks. The system may receive a template edit check (TEC) and a parameter set (step 602). The system may determine whether multiple parameters are described in the TEC (step 604). The system may determine whether the parameter type is an array (step 606). In response to determining an array parameter type, the system may store the unique depth of the array element in a depths array associated with the parameter (step 608). Otherwise, the process will return to step 604. The system may determine whether any element depths are associated with the parameter (step 610). In response to determining an associate depth, the system may generate a dynamic code (step 612). The system may execute the generated dynamic code (step 614) and end. In response to determining no associated depth, the system may queue the template edit check for processing (step 616). The system may check for additional non-array parameters (step 618). In response to determining no more non-array parameters the process may end. Otherwise, the system may process the arrays to generate the plurality of edit checks (step 620). The system may store the generated edit checks in the database 116 (step 622).

In various embodiments, the system may generate an edit check extraction report comprising a table of object IDs, edit levels, target paths, edit actions, and expressions. The system may generate the template edit check based on the edit check extraction report. In various embodiments, the target paths may be associated with target types. The system may match instances where the edit level, target type, edit action, and expression, and item references are closely related. In this regard, the system may enable generation of the template edit check based on relatedness of the edit check set. For example, the system may highlight the edit checks below:

| EditLevel | TargetPath | EditAction | Expression |
|---|---|---|---|
| Patient | [New Patient][Cohort 3_Month 60.*][CT.*] | Hidden | !isEmpty([New Patient][Cohort 3_Month 60][VISIT][Visit][VISITND]) |
| Patient | [New Patient][Day 42_Week 6.*][BIO.*] | Hidden | !isEmpty([New Patient][Day 42_Week 6][VISIT][Visit][VISITND]) |

In the example of paragraph [0045] the target path is of the type [Patient][Visit][Form] and the expression is referenced the same, e.g., [Form][Group][Item]=[VISIT][Visit][VISITND]. The variables between the two edit checks are the target forms ([CT] and [BIO]) and the target and source visits references ([Cohort 3_Month 60] and [Day 42_Week 6]). In this regard, the system may generate a template edit check comprising a list of forms and a list of visits based on the highlighted relationship.

In another example, the system may highlight the edit checks below:

| EditLevel | TargetPath | EditAction | Expression | Data Expression |
|---|---|---|---|---|
| Patient | [New Patient][Month 45.*][VISIT.*][Visit.*][VISIT] | Data Value Advice | TRUE | 'Month 45' |
| Patient | [New Patient][Month 48.*][VISIT.*][Visit.*][VISIT] | Data Value Advice | TRUE | 'Month 48' |
| Patient | [New Patient][Month 51.*][VISIT.*][Visit.*][VISIT] | Data Value Advice | TRUE | 'Month 51' |
| Patient | [New Patient][Month 54.*][VISIT.*][Visit.*][VISIT] | Data Value Advice | TRUE | 'Month 54' |
| Patient | [New Patient][Month 57.*][VISIT.*][Visit.*][VISIT] | Data Value Advice | TRUE | 'Month 57' |
| Patient | [New Patient][Month 60.*][VISIT.*][Visit.*][VISIT] | Data Value Advice | TRUE | 'Month 60' |
| Patient | [New Patient][End of Assessment Visit.*][VISIT.*][Visit.*][VISIT] | Data Value Advice | TRUE | 'End of Assessment Visit' |
| Patient | [New Patient][Cohort 3_Screening.*][VISIT.*][Visit.*][VISIT] | Data Value Advice | TRUE | 'Cohort 3_Screening' |

In the example of paragraph [0048], the 'Data Expression' may be a string and the visit may be a variable. In this regard the system may enable determination of a template parameter: @vistis, LIST OF VISITS, {[Month 45], [Month48] . . . [Month 60]}, depth 1. Thereby the system may enable a template edit check comprising: Patent, Target Level=item, Target=[New Patient][@Visits. *][VISIT. *][Visit. *][VISIT], Action Exp=TRUE, Data Exp='@Visits'.

The metadata for the particular study preferably identifies the data that is to be collected and is used for defining the edit check template. As mentioned above, when generating the edit checks to software uses a template edit check and one or more parameters. For example, a relatively simple template edit check without any "array" parameters, but where the user/study designer wants to externalize the standard values for easier copying between clinical trials/studies, may be defined in one non-limiting embodiment of pseudocode in the table below:

| High BP test | Valid: edit check. Message = High BP |
|---|---|
| Target | [VS][SYSBP] |
| Template Edit | [VS][SYSBP] > @SYSBP ‖ [VS][DIABP] > @DIABP |
| Parameters | @SYSBP = 120; @DIABP=80 |

With reference to the table of paragraph [0051], there may be two (2) parameters with no depths. Therefore, for each parameter the parameters reference in the edit check can be replaced with a parameter value. Applying process 600, the generated edit check for this non-limiting example may be: "[VS][SYSBP]>120‖[VS][DIABP]>80"

With reference to steps 610-614, where a parameter has depth, the code can be preferably generated via dynamic code. Where there are multiple arrays with different "depth", code is generated for replacing the variables. One non-limiting example for such code can include the below pseudocode:

```
For d=1..# of arrays with different depth.
    Block1 = block1 + "Loop a<d> where array.depth = <d>"
    Block2 = block2 + "replace(text, prm(a<d>).name, prm(a<d>).value)"
    Block3 = block3 + "end loop"
End loop
genCode = block1 + block2 +
"Loop x=1..Prm.len where type != 'ARRAY'"
+ "Replace (genEdit, Prm(x).name, Prm(x).value)"
+ "end loop"
+ "Save generated edit check"
```

In another example of process 600, consider the template edit check and parameter set below:
Template edit check

| Target Path | [New Subject][@DAYVISITS.*][@DAYFORMS.*] |
|---|---|
| Edit Level | Patient |
| Edit Action | Hidden |
| Expression | !isEmpty([New Subject][@DAYVISITS][VISIT][Visit][VISITND]) |

Parameter set

| Param | Type | Mapping | Depth | Description |
|---|---|---|---|---|
| @DAYVISITS | Array | 'DAY 0', 'DAY 14', 'DAY 28', 'DAY 56', 'DAY 84' | 1 | Visits starting with DAY |
| @DAYFORMS | Array | 'EG', 'PA', 'VS', 'EX', 'SD', 'DLQI', 'SF36', 'CD' | 2 | Forms within each DAY visit |

Considering now the pseudo code of paragraphs [0060-0095] below, process 600 having inputs of the template edit check and parameter set described in paragraphs [0057] and [0058] may generate (by dynamic code generator module 112) the dynamic code at paragraphs [0077-0088] via steps 610-614.

```
Record Params (
    Name text
    , Type text
    , Value [text|Number|Array]
    , Depth int -- Only used for Array types
)
Parameters table_of_params
Depths table_of_Int
Proc (Template text, Prm Parameters)
genEdit text
Loop y=1..Prm.len
    if Prm(y).Type = 'ARRAY'
        Depths(Prm(y).Depth) = Prm(y).Depth -- Distinct Depths in array parameters
    end if
end loop
IF Depths.len > 0
Loop a1=Arrays where Depth=1
    Loop a2=Arrays where Depth=2
        genEdit = Template
        Replace (genEdit, Prm(a1).name, Prm(a1).value)
        Replace (genEdit, Prm(a2).name, Prm(a2).value)
        Loop x=1..Prm.len where type != 'ARRAY'
            Replace (genEdit, Prm(x).name, Prm(x).value)
        end loop
        SAVE genEdit
    end loop
end loop
ELSE
    genEdit = Template
    Loop x=1..Prm.len
        Replace (genEdit, Prm(x).name, Prm(x).value)
```

-continued

```
    end loop
    SAVE genEdit
END IF
```

In the above non-limiting example, the generated code has one loop as there are two arrays with a different depth specified. Preferably, it may be assumed that depth is in order (e.g. {1,2} not {1,3}). In the non-limiting example and with reference to steps 618-622, the system can automatically electronically generate the following forty edit checks (@DAYVISITS has 5 elements and @DAYFORMS has 8 elements; 5*8=40), as shown below and, in this regard tends to eliminate the need for the manually generating each of these edit checks.

Generated edit checks

| Target Path | [New Subject][DAY 0.*][EG.*] |
|---|---|
| Expression | !isEmpty([New Subject][DAY 0][VISIT][Visit][VISITND]) |

| Target Path | [New Subject][DAY 0.*][PA.*] |
|---|---|
| Expression | !isEmpty([New Subject][DAY 0][VISIT][Visit][VISITND]) |

| Target Path | [New Subject][DAY 0.*][VS.*] |
|---|---|
| Expression | !isEmpty([New Subject][DAY 0][VISIT][Visit][VISITND]) |

| Target Path | [New Subject][DAY 0.*][SD.*] |
|---|---|
| Expression | !isEmpty([New Subject][DAY 0][VISIT][Visit][VISITND]) |

| Target Path | [New Subject][DAY 14.*][EG.*] |
|---|---|
| Expression | !isEmpty([New Subject][DAY 14][VISIT][Visit][VISITND]) |

In another example of process 600, consider the template edit check and parameter set below:

Template edit check.

| Target Path | [New Subject][@VISITS.*][VISIT.*][Visit.*][Expected Visit Date] |
|---|---|
| Edit Level | Item |
| Edit Action | DVA |
| Expression | var date=[New Subject][DAY 0][VISIT][Visit][VISDAT]; |
| | var numDay=@VISITDAYS; |
| | if(!isEmpty(date)) |
| | AddDaysToDate(date,numDay) |
| | else |
| | " |

Parameter set

| Parameter | Type | Mapping | Depth | Description |
|---|---|---|---|---|
| @VISITS | Array | 'DAY 14', 'DAY 28', 'DAY 56', 'DAY 84' | 1 | Visits starting with DAY 14 |
| @VISITDAYS | Array | 14, 28, 56, 84 | 1 | Visit days offset from DAY 0 |

Considering now the pseudo code of paragraphs [0102-0135] below, process 600 having inputs of the template edit check and parameter set described in paragraphs [0099] and [0100] may generate the dynamic code at paragraphs [0119-0128] via steps 610-614.

```
Record Params (
   Name text
 , Type text
 , Value [text|Number|Array]
 , Depth int -- Only used for Array types
 )
Parameters table_of_params
Depths table_of_Int
Proc (Template text, Prm Parameters)
genEdit text
Loop y=1..Prm.len
     if Prm(y).Type = 'ARRAY'
         Depths(Prm(y).Depth) = Prm(y).Depth -- Distinct Depths in array parameters
     end if
end loop
IF Depths.len > 0
     -- Generate dynamic code: For example if 1 depths the code would be
     Loop a1=Arrays where Depth=1
         genEdit = Template
```

```
         Replace (genEdit, Prm(a1).name, Prm(a1).value)
         Loop x=1..Prm.len where type != 'ARRAY'
             Replace (genEdit, Prm(x).name, Prm(x).value)
         end loop
         SAVE genEdit
     end loop
ELSE
     genEdit = Template
     Loop x=1..Prm.len
         Replace (genEdit, Prm(x).name, Prm(x).value)
     end loop
     SAVE genEdit
END IF
```

In the above non-limiting example, the generated code has one loop as there are two arrays both with depth=1. Preferably, it may be assumed that arrays with the same depth have or always have the same number of elements. In the non-limiting example and with reference to steps 618-622, the system can automatically electronically generate the following four edit checks and, in this regard tends to eliminate the need for the manually generating each of these edit checks.

Generated edit checks

| Target Path | [New Subject][DAY 14.*][VISIT.*][Visit.*][Expected Visit Date] |
|---|---|
| Expression | var date=[New Subject][DAY 0][VISIT][Visit][VISDAT];<br>var numDay=14;<br>if(!isEmpty(date))<br>AddDaysToDate(date,numDay)<br>else<br>" |

| Target Path | [New Subject][DAY 28.*][VISIT.*][Visit.*][Expected Visit Date] |
|---|---|
| Expression | var date=[New Subject][DAY 0][VISIT][Visit][VISDAT];<br>var numDay=28;<br>if(!isEmpty(date))<br>AddDaysToDate(date,numDay)<br>else<br>" |

| Target Path | [New Subject][DAY 56.*][VISIT.*][Visit.*][Expected Visit Date] |
|---|---|
| Expression | var date=[New Subject][DAY 0][VISIT][Visit][VISDAT];<br>var numDay=56;<br>if(!isEmpty(date))<br>AddDaysToDate(date,numDay)<br>else<br>" |

| | |
|---|---|
| Target Path | [New Subject][DAY 84.*][VISIT.*][Visit.*][Expected Visit Date] |
| Expression | var date=[New Subject][DAY 0][VISIT][Visit][VISDAT];<br>var numDay=84;<br>if(!isEmpty(date))<br>AddDaysToDate(date,numDay)<br>else<br>" |

As discussed above, the system may receive parameter sets and template edit checks from the user device 104. For example, the user may construct template edit checks via a user interface of the runtime module 108. With additional reference to FIG. 7 a template construction interface 700 of system 100 is illustrated in accordance with various embodiments. The interface 700 includes an action expression field 702, a code list 704 including tabs for items, functions, and parameters, a variables data table 706, and a generate edit check button 708. In various embodiments the code list 704 may be searchable. For example, a search field 710 may be configured to receive text based search inputs.

Figure 8:
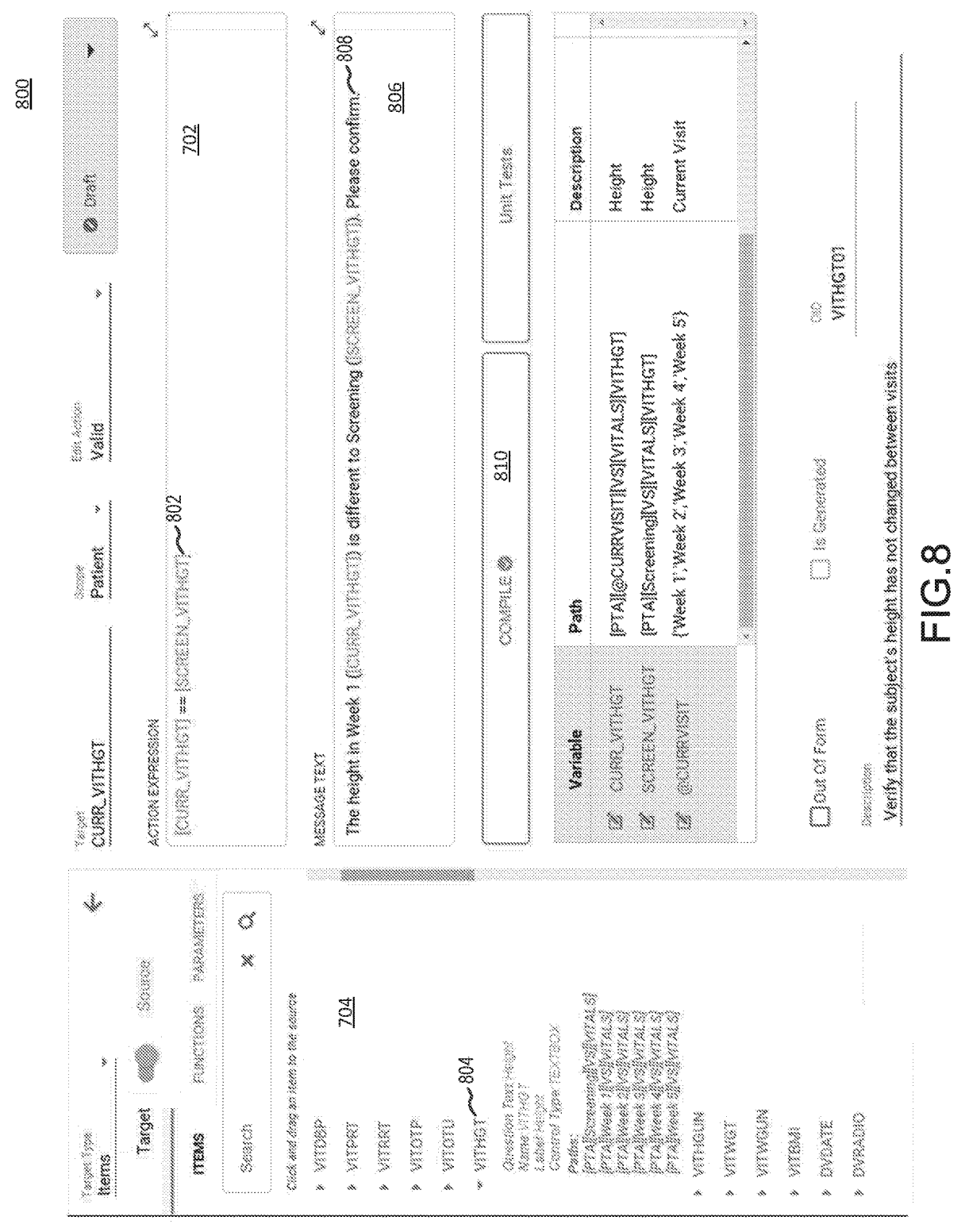

With additional reference to FIG. 8, a template validation interface 800 of system 100 is illustrated in accordance with various embodiments. Interface 800 displays the action expression 802 in the action expression field 702 which has been constructed from selecting items 804 from code list 704. The system may display a message text field 806 and a message text 808 associated with the action expression 802. Interface 800 includes a compile action button 810 which may command the system to compile the action expression 802 in response to registering a user interaction from the user device 104. In response to compiling the action expression, the system may display one or more errors and prompt the user via the user device 104 to correct the compilation errors.

Figure 9:
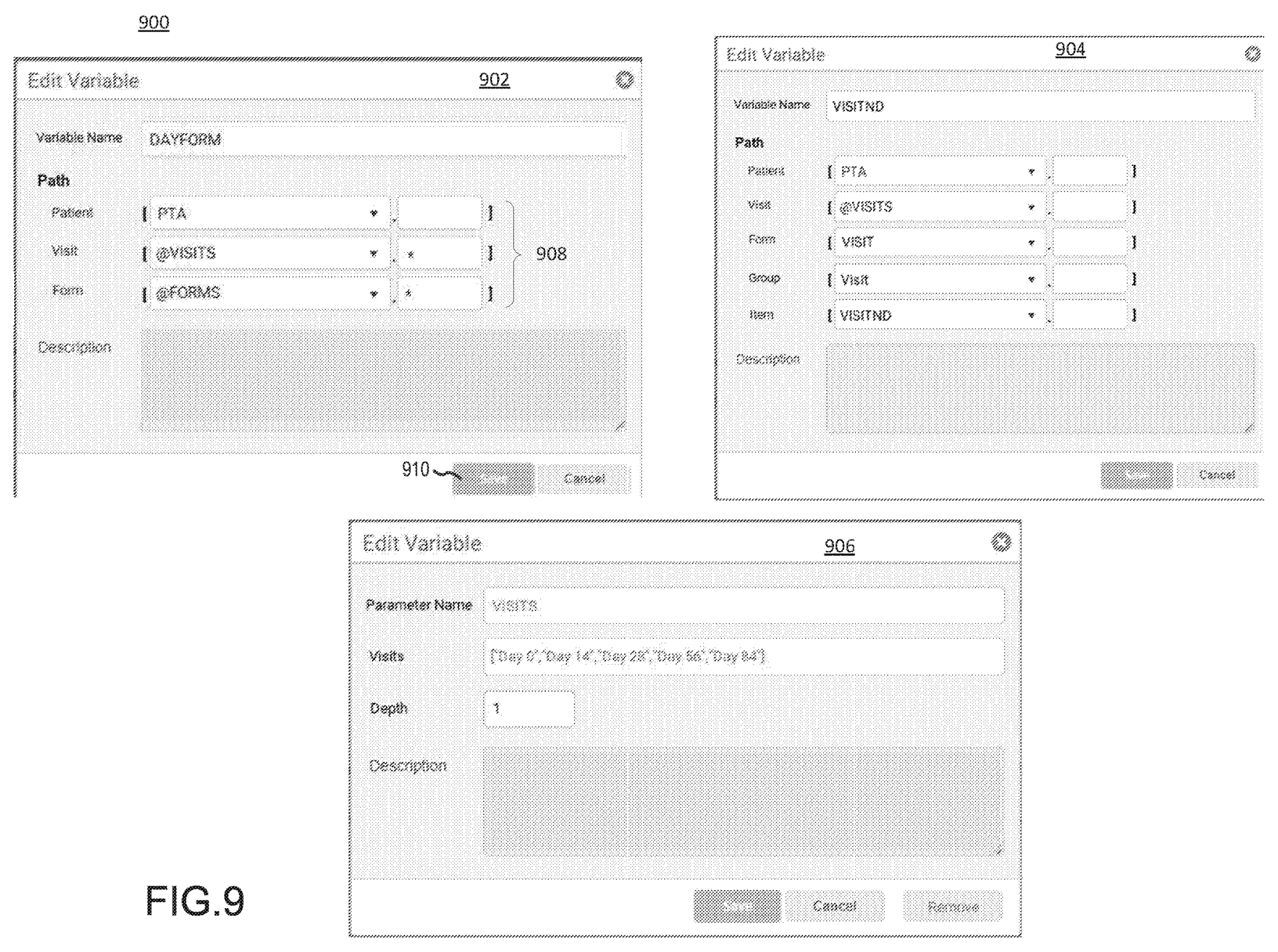

With additional reference to FIG. 9, variables data editing interfaces 900 of system 100 are illustrated in accordance with various embodiments. The system may display variable specific interfaces for each variable type such as, for example, a first variable type interface 902, a second variable type interface 904, and a parameter type interface 906. In various embodiments, each of the specific interfaces (902, 904, 906) may be displayed in response to receiving an interaction with the associated variable 712 of the variables data table 706. For example, the first variable type interface 902 may be displayed in response to receiving an interaction (e.g., user clicks on) with the "DAYFORM" variable 712 of the variables data table 706. The first variable type interface 902 may display one or more selectable and editable path parameters 908 as defined by the data structure (e.g., FIG. 2). In this regard the system may enable editing of values related to the selected variable. The edits may be saved in response the system receiving an interaction from a save button 910.

Figure 10:
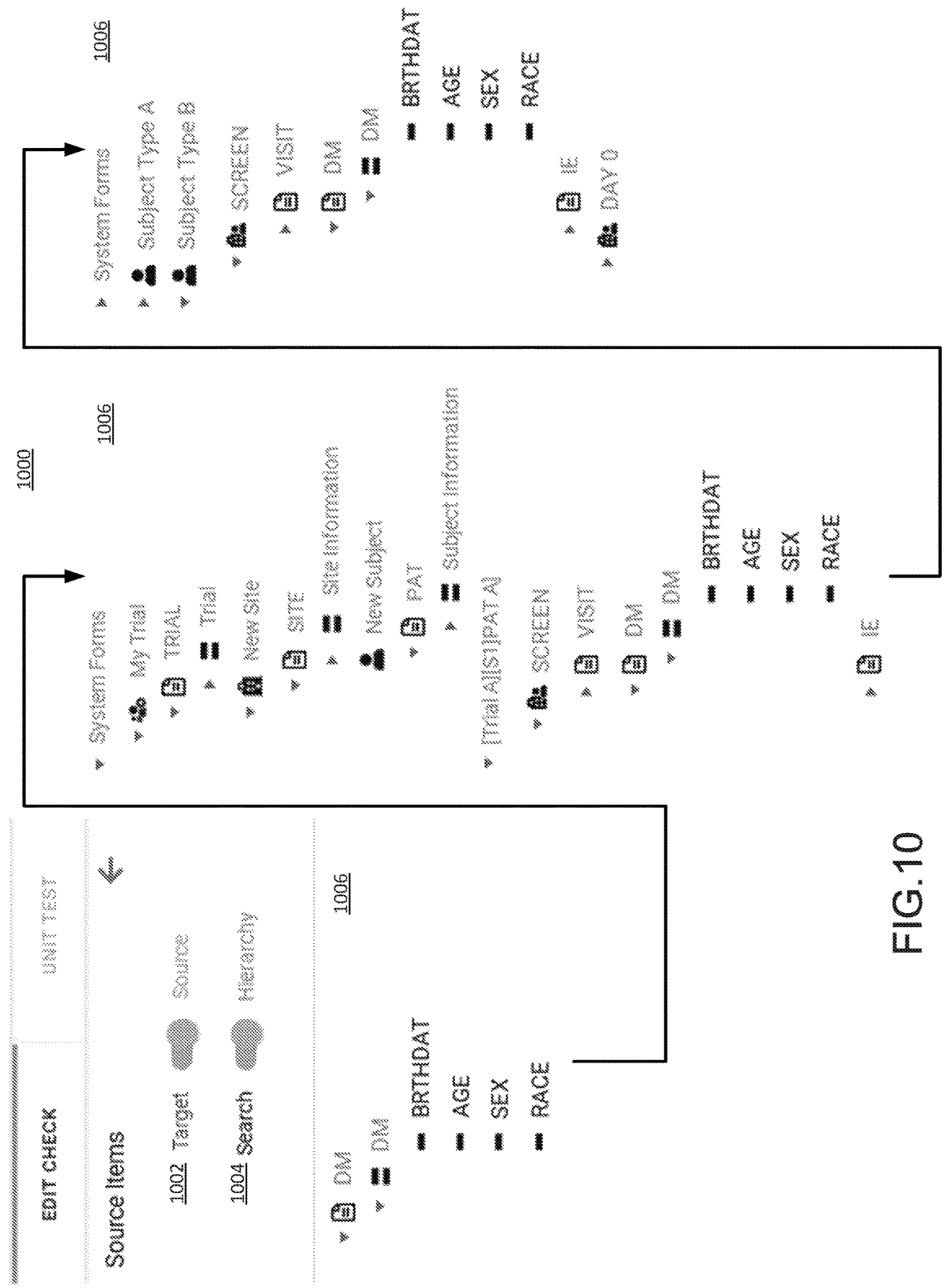
FIG. 10 illustrates a hierarchical view of trial objects in a system for automated edit check generation, in accordance with various embodiments.

With additional reference to FIG. 10, a hierarchical view of trial objects 1000 used in edit checks of system 100 are illustrated in accordance with various embodiments. The system may receive a user interaction such as, for example, via a target-source switch 1002 or a search-hierarchy switch 1004. In response, the system may display an object hierarchy 1006. The object hierarch 1006 may be interactive and expandable. For example, the 'DM' group may be selected and expand to display the items 'birthdat', 'age', 'sex', and 'race'. In various embodiments, the object hierarchy 1006 may include higher level associations such as 'system forms' and 'trials' which may be displayed collapsed by default or hidden. For example, if the scope is 'site' the top node may be [S1][PAT 1] and the trial level may not be available under patient forms. In various embodiments, multiple patient types (e.g., Subject Type A, Subject Type B, etc.) may be associated with a trial and/or a site.

As discussed herein, existing codelists or reference data may be used as In Lists or Arrays to reduce, if not eliminate, duplicating data. The In List and Arrays can be created from system defines lists so that such information does not need to be manually reentered by the study designer/user. In various embodiments, the reference information can be maintained as a soft reference, such that template parameters can be copied from one study to another study. In various embodiments, system lists may include, for example, visits, forms, forms with visits, groups, groups within a form, items, items within a group, etc.

For In List Item References, preferably variable names can be used as parameters to permit more generic library code for reuse. With respect to array loops, previously multiple edit checks can be automatically generated based on array parameters resulting in fewer unique checks having to be written by the user/designer. Preferably, array references with a same depth specified can have same number elements. In one non-limiting example, array loops of up to 3 levels deep can be used, though other values can be used and are considered within the scope of the disclosure.

Where a Target does not contain a loop, preferably none of the expressions will reference an array. Here the expressions can reference either an array pointer in Target or can use the pointer within an array in the expression. Preferably, parameters will be included in messages in order to provide more informative error messages to the user. During the study design process, a check can be switched off, as opposed to deleting it, in order to maintain higher reuse between studies. This can be implemented through a disable property on the edit check property.

Preferably during the design, the existence of a parameter can be checked in order to allow the developer/designer to write/generate more generic code not requiring all template parameters to be present. When generating edit checks from a template edit check, preferably any error can be made known to the developer/designer in order to correct or fix the error.

Preferably, the edit check template parameters can be unique within a study so that they can rely on sematic interoperability when copying template parameters between studies. Preferably, the template parameter is unique by name only, since its values can change often from trial to trial. A description record may be created of what the intent of the object is, to permit others to re-use these objects, for one or more of the created template parameters, template edit checks or edit checks. In various embodiments, the description record may be stored as rules data 122.

In various embodiments, it can be specified which trials may permit copy operations and which trial developers/ designers may be permitted to copy objects. In one non-limiting embodiment, the copy operation can be invoked by keyboard or menu and objects can be selected for copying to a clipboard. Non-limiting examples for the copying operation can include: (1) Multi-select objects to copy from the tree; (2) Select one or more edits from Edit validation popup targeting a single object; (3) Select one or more edits from Edit search screen; (4) Select one or more objects from object search screen; (5) Select one or more Client Functions; and (6) If no selection is made to copy, then warn user to select. Selected objects can be pasted from the clipboard in the target trial group where permission has been granted.

In various embodiments, the runtime module 108 user interface enables a person's particular template edit check(s) to be searched from amongst all template edit checks, in order to improve work efficiency. Preferably, template parameters can be searched, such as by caption/description and by the template edit checks themselves. Preferably, when developing a clinical trial, edit checks can be generated and tested from a same user interface that the template edit checks are developed from, though such is not considered limiting. Preferably, any changes made to template or parameters after the edits have been generated can be kept track of to permit regeneration of the edits to reconcile any changes made to the template edits. The last changes can be stored and time stamped, and a user id can also be stored, on all template and edit records to permit changes to be tracked to edit definitions from a specific time point.

In various embodiments, an edit change report may also be generated by the system and displayed for review. The change report may be customizable and can be based on different criteria. In this regard, the system may permit a developer to compare and review changes and adjust them where inconsistencies with requirements are found or for duplicate or potential looping issues. Filter changes can be based on time, last protocol amendment (e.g., Mid-Study Change) or last edit generation. In various embodiments, a template parameter can be created which can store the parent object and can loop through all children present in it during the time of edit generation, to allow for continual adding/deleting children under the referenced parent without having to update the template parameter.

In various embodiments, the reference edits may be unique within a trial, though such is not considered limiting. A reference edit may be defined to be unique by its action type, target path and action expression. Once the reference edit is added it can be uniquely identified by its OID. During a copy operation, the comparison can be made based on definition uniqueness and an OID can be renamed if a conflict is found. In various embodiments, inlist sourced from codelists can be created to eliminate having to manually type the values of the inlist. Preferably, the developer/user can choose which items from the codelist belongs to the inlist.

In various embodiments, objects from another trial may be selected via the user interface and copied to the user/designer/developer's working trial. The user's story can focus on the framework for searching, displaying and selecting objects from other trials. A lookup control can be provided to relatively quickly review external trials. Preferably, objects that can be inserted in the destination object are allowed to be selected and copied. A lookup panel can display selected objected properties to allow the user/developer to review.

In like regard, template parameters from another trial (source) can also be copied to a working (target) trial to allow the template parameters to be reused across trials. As template parameters preferably are unique across trials, preferably the system can either not allow for selection of template parameters in the source which exists in the trial or have the copy process show a warning that at least certain parameters were not copied. As the template parameters can be preferably used for edit check generation, both the definition and mapping values can be preferably copied without creating an error condition. Preferably, the uniqueness criteria (defined by the name of the template parameter) can be followed.

In various embodiments, template edit check from another trial (source) may also be copied to the working trial (target) so they may be reused across trials. The following behavior may be expected (1) include Client functions and template parameters; (2) provide warning during copying if any object already exists and the definition is different; and (3) uniqueness based on Action type, Target Path and Action expression and the OID can be renamed if a conflict is found in the target trial.

In various embodiments, forms from another trial (source) may also be copied to the working trial (target) so the definition does not have to be retyped. The following objects may be included when copying the form if they don't already existing in the target trial: (1) form; (2) group(s); (3) items—codelist can be used; (4) edit checks—those which are preferably not cloned or generated, and will compile; and (5) template edit checks generating checks for the form—template parameters. In various embodiments, the edit checks may be automatically regenerated by the edit check generator 110 where the template edit check, parameters or parameters' value(s) change such that the generated edit check are preferably the latest version.

In various embodiments, the system may also be designed or programmed to prevent a MSC/Migrate where there is an invalid template edit checks or if invalid generated edit checks exist. For example, the reference edits, templates and parameters can travel with the study XML, to allow them to be copies over to another study or across environments. In various embodiments, the system can warn the user or developer if there are invalid reference edits checks or if invalid generated edit checks exist. For example, where a developer changes an item or codelist property, a warning may be generated and displayed by the runtime module 108 of all reference edits, templates and template parameters that will be affected to allow the developer to fix them for regeneration.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. § 112(f) unless the element is expressly recited using the phrase "means for" or "step for". As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Terms and phrases similar to "associate" and/or "associating" may include tagging, flagging, correlating, using a look-up table or any other method or system for indicating or creating a relationship between elements. Moreover, the associating may occur at any point, in response to any suitable action, event, or period of time. The associating may occur at pre-determined intervals, periodically, randomly, once, more than once, or in response to a suitable request or action. Any of the information may be distributed and/or accessed via a software enabled link, wherein the link may be sent via an email, text, post, social network input, and/or any other method known in the art.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In re Nuijten to fall outside the scope of patentable subject matter under 35 U.S.C. § 101.

In various embodiments, components, modules, and/or engines of system 100 may be implemented as micro-applications or micro-apps. Micro-apps are typically deployed in the context of a mobile operating system, including for example, a WINDOWS® mobile operating system, an ANDROID® operating system, an APPLE® iOS operating system, a BLACKBERRY® company's operating system, and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

The system and method may be described herein in terms of functional block components, screen shots, optional selections, and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, JAVA®, JAVASCRIPT®, JAVASCRIPT® Object Notation (JSON), VBScript, Macromedia COLD FUSION, COBOL, MICROSOFT® company's Active Server Pages, assembly, PERL®, PHP, awk, PYTHON®, Visual Basic, SQL Stored Procedures, PL/SQL, any UNIX® shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT®, VBScript, or the like.

The system and method are described herein with reference to screen shots, block diagrams and flowchart illustrations of methods, apparatus, and computer program products according to various embodiments. It will be understood that each functional block of the block diagrams and the flowchart illustrations, and combinations of functional blocks in the block diagrams and flowchart illustrations, respectively, can be implemented by computer program instructions Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS® applications, webpages, websites, web forms, prompts, etc. Practitioners will appreciate that the illustrated steps described herein may comprise, in any number of configurations, including the use of WINDOWS® applications, webpages, web forms, popup WINDOWS® applications, prompts, and the like. It should be further appreciated that the multiple steps as illustrated and described may be combined into single webpages and/or WINDOWS® applications but have been expanded for the sake of simplicity. In other cases, steps illustrated and described as single process steps may be separated into multiple webpages and/or WINDOWS® applications but have been combined for simplicity.

In various embodiments, the software elements of the system may also be implemented using a JAVASCRIPT® run-time environment configured to execute JAVASCRIPT® code outside of a web browser. For example, the software elements of the system may also be implemented using NODE.JS® components. NODE.JS® programs may implement several modules to handle various core functionalities. For example, a package management module, such as NPM®, may be implemented as an open source library to aid in organizing the installation and management of third-party NODE.JS® programs. NODE.JS® programs may also implement a process manager, such as, for example, Parallel Multithreaded Machine ("PM2"); a resource and performance monitoring tool, such as, for example, Node Application Metrics ("appmetrics"); a library module for building user interfaces, and/or any other suitable and/or desired module.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the internet server. Middleware may be configured to process transactions between the various components of an application server and any number of internal or external systems for any of the purposes disclosed herein. WEBSPHERE® MQTM (formerly MQSeries) by IBM®, Inc. (Armonk, NY) is an example of a commercially available middleware product. An Enterprise Service Bus ("ESB") application is another example of middleware The computers discussed herein may provide a suitable website or other internet-based graphical user interface which is accessible by users. In one embodiment, MICROSOFT® company's Internet Information Services (IIS), Transaction Server (MTS) service, and an SQL SERVER® database, are used in conjunction with MICROSOFT® operating systems, WINDOWS NT® web server software, SQL SERVER® database, and MICROSOFT® Commerce Server. Additionally, components such as ACCESS® software, SQL SERVER® database, ORACLE® software, SYBASE® software, INFORMIX® software, MYSQL® software, INTERBASE® software, etc., may be used to provide an Active Data Object (ADO) compliant database management system. In one embodiment, the APACHE® web server is used in conjunction with a LINUX® operating system, a MYSQL® database, and PERL®, PHP, Ruby, and/or PYTHON® programming languages.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

In various embodiments, the system and various components may integrate with one or more smart digital assistant technologies. For example, exemplary smart digital assistant technologies may include the ALEXA® system developed by the AMAZON® company, the GOOGLE HOME® system developed by Alphabet, Inc., the HOMEPOD® system of the APPLE® company, and/or similar digital assistant technologies. The ALEXA® system, GOOGLE HOME® system, and HOMEPOD® system, may each provide cloud-based voice activation services that can assist with tasks, entertainment, general information, and more. All the ALEXA® devices, such as the AMAZON ECHO®, AMAZON ECHO DOT®, AMAZON TAP®, and AMAZON FIRE® TV, have access to the ALEXA® system. The ALEXA® system, GOOGLE HOME® system, and HOMEPOD® system may receive voice commands via its voice activation technology, activate other functions, control smart devices, and/or gather information. For example, the smart digital assistant technologies may be used to interact with music, emails, texts, phone calls, question answering, home improvement information, smart home communication/activation, games, shopping, making to-do lists, setting alarms, streaming podcasts, playing audiobooks, and providing weather, traffic, and other real time information, such as news. The ALEXA®, GOOGLE HOME®, and HOMEPOD® systems may also allow the user to access information about eligible transaction accounts linked to an online account across all digital assistant-enabled devices.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., WINDOWS®, UNIX®, LINUX®, SOLARIS®, MACOS®, etc.) as well as various conventional support software and drivers typically associated with computers.

The present system or any part(s) or function(s) thereof may be implemented using hardware, software, or a combination thereof and may be implemented in one or more computer systems or other processing systems. However, the manipulations performed by embodiments may be referred to in terms, such as matching or selecting, which are commonly associated with mental operations performed by a human operator. No such capability of a human operator is necessary, or desirable, in most cases, in any of the operations described herein. Rather, the operations may be machine operations or any of the operations may be conducted or enhanced by artificial intelligence (AI) or machine learning. AI may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices.

In various embodiments, the embodiments are directed toward one or more computer systems capable of carrying out the functionalities described herein. The computer system includes one or more processors. The processor is connected to a communication infrastructure (e.g., a communications bus, cross-over bar, network, etc.). Various software embodiments are described in terms of this exemplary computer system. After reading this description, it will become apparent to a person skilled in the relevant art(s) how to implement various embodiments using other computer systems and/or architectures. The computer system can include a display interface that forwards graphics, text, and other data from the communication infrastructure (or from a frame buffer not shown) for display on a display unit.

The computer system also includes a main memory, such as random access memory (RAM), and may also include a secondary memory. The secondary memory may include, for example, a hard disk drive, a solid-state drive, and/or a removable storage drive. The removable storage drive reads from and/or writes to a removable storage unit in a well-known manner. As will be appreciated, the removable storage unit includes a computer usable storage medium having stored therein computer software and/or data.

In various embodiments, secondary memory may include other similar devices for allowing computer programs or other instructions to be loaded into a computer system. Such devices may include, for example, a removable storage unit and an interface. Examples of such may include a program cartridge and cartridge interface (such as that found in video game devices), a removable memory chip (such as an erasable programmable read only memory (EPROM), programmable read only memory (PROM)) and associated socket, or other removable storage units and interfaces, which allow software and data to be transferred from the removable storage unit to a computer system.

The terms "computer program medium," "computer usable medium," and "computer readable medium" are used to generally refer to media such as removable storage drive and a hard disk installed in hard disk drive. These computer program products provide software to a computer system.

The computer system may also include a communications interface. A communications interface allows software and data to be transferred between the computer system and external devices. Examples of such a communications interface may include a modem, a network interface (such as an Ethernet card), a communications port, etc. Software and data transferred via the communications interface are in the form of signals which may be electronic, electromagnetic, optical, or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

In various embodiments, the server may include application servers (e.g., WEBSPHERE®, WEBLOGIC®, JBOSS®, POSTGRES PLUS ADVANCED SERVER®, etc.). In various embodiments, the server may include web servers (e.g., Apache, IIS, GOOGLE® Web Server, SUN JAVA® System Web Server, JAVA® Virtual Machine running on LINUX® or WINDOWS® operating systems).

A web client includes any device or software which communicates via any network, such as, for example any device or software discussed herein. The web client may include internet browsing software installed within a computing unit or system to conduct online transactions and/or communications. These computing units or systems may take the form of a computer or set of computers, although other types of computing units or systems may be used, including personal computers, laptops, notebooks, tablets, smart phones, cellular phones, personal digital assistants, servers, pooled servers, mainframe computers, distributed computing clusters, kiosks, terminals, point of sale (POS) devices or terminals, televisions, or any other device capable of receiving data over a network. The web client may include an operating system (e.g., WINDOWS®, WINDOWS MOBILE® operating systems, UNIX® operating system, LINUX® operating systems, APPLE® OS® operating systems, etc.) as well as various conventional support software and drivers typically associated with computers. The web-client may also run MICROSOFT® INTERNET EXPLORER® software, MOZILLA® FIREFOX® software, GOOGLE CHROME™ software, APPLE® SAFARI® software, or any other of the myriad software packages available for browsing the internet.

As those skilled in the art will appreciate, the web client may or may not be in direct contact with the server (e.g., application server, web server, etc., as discussed herein). For example, the web client may access the services of the server through another server and/or hardware component, which may have a direct or indirect connection to an internet server. For example, the web client may communicate with the server via a load balancer. In various embodiments, web client access is through a network or the internet through a commercially-available web-browser software package. In that regard, the web client may be in a home or business environment with access to the network or the internet. The web client may implement security protocols such as Secure Sockets Layer (SSL) and Transport Layer Security (TLS). A web client may implement several application layer protocols including HTTP, HTTPS, FTP, and SFTP.

The various system components may be independently, separately, or collectively suitably coupled to the network via data links which includes, for example, a connection to an Internet Service Provider (ISP) over the local loop as is typically used in connection with standard modem communication, cable modem, DISH NETWORK®, ISDN, Digital Subscriber Line (DSL), or various wireless communication methods. It is noted that the network may be implemented as other types of networks, such as an interactive television (ITV) network. Moreover, the system contemplates the use, sale, or distribution of any goods, services, or information over any network having similar functionality described herein.

The system contemplates uses in association with web services, utility computing, pervasive and individualized computing, security and identity solutions, autonomic computing, cloud computing, commodity computing, mobility and wireless solutions, open source, biometrics, grid computing, and/or mesh computing.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® applets, JAVASCRIPT® programs, active server pages (ASP), common gateway interface scripts (CGI), extensible markup language (XML), dynamic HTML, cascading style sheets (CSS), AJAX (Asynchronous JAVASCRIPT And XML)

programs, helper applications, plug-ins, and the like. A server may include a web service that receives a request from a web server, the request including a URL and an IP address (192.168.1.1). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. For example, representational state transfer (REST), or RESTful, web services may provide one way of enabling interoperability between applications.

The computing unit of the web client may be further equipped with an internet browser connected to the internet or an intranet using standard dial-up, cable, DSL, or any other internet protocol known in the art. Transactions originating at a web client may pass through a firewall in order to prevent unauthorized access from users of other networks. Further, additional firewalls may be deployed between the varying components of CMS to further enhance security.

Encryption may be performed by way of any of the techniques now available in the art or which may become available—e.g., Twofish, RSA, El Gamal, Schorr signature, DSA, PGP, PM, GPG (GnuPG), HPE Format-Preserving Encryption (FPE), Voltage, Triple DES, Blowfish, AES, MD5, HMAC, IDEA, RC6, and symmetric and asymmetric cryptosystems. The systems and methods may also incorporate SHA series cryptographic methods, elliptic curve cryptography (e.g., ECC, ECDH, ECDSA, etc.), and/or other post-quantum cryptography algorithms under development.

The firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based, access control lists, and Packet Filtering among others. Firewall may be integrated within a web server or any other CMS components or may further reside as a separate entity. A firewall may implement network address translation ("NAT") and/or network address port translation ("NAPT"). A firewall may accommodate various tunneling protocols to facilitate secure communications, such as those used in virtual private networking. A firewall may implement a demilitarized zone ("DMZ") to facilitate communications with a public network such as the internet. A firewall may be integrated as software within an internet server or any other application server components, reside within another computing device, or take the form of a standalone hardware component.

Any databases discussed herein may include relational, hierarchical, graphical, blockchain, object-oriented structure, and/or any other database configurations. Any database may also include a flat file structure wherein data may be stored in a single file in the form of rows and columns, with no structure for indexing and no structural relationships between records. For example, a flat file structure may include a delimited text file, a CSV (comma-separated values) file, and/or any other suitable flat file structure. Common database products that may be used to implement the databases include DB2® by IBM® (Armonk, NY), various database products available from ORACLE® Corporation (Redwood Shores, CA), MICROSOFT ACCESS® or MICROSOFT SQL SERVER® by MICROSOFT® Corporation (Redmond, Washington), MYSQL® by MySQL AB (Uppsala, Sweden), MONGODB®, Redis, APACHE CASSANDRA®, HBASE® by APACHE®, MapR-DB by the MAPR® corporation, or any other suitable database product. Moreover, any database may be organized in any suitable manner, for example, as data tables or lookup tables. Each record may be a single file, a series of files, a linked series of data fields, or any other data structure.

As used herein, big data may refer to partially or fully structured, semi-structured, or unstructured data sets including millions of rows and hundreds of thousands of columns. A big data set may be compiled, for example, from a history of patient records over time, from web registrations, from social media, from records of charge (ROC), from summaries of charges (SOC), from internal data, or from other suitable sources. Big data sets may be compiled without descriptive metadata such as column types, counts, percentiles, or other interpretive-aid data points.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); data stored as Binary Large Object (BLOB); data stored as ungrouped data elements encoded using ISO/IEC 7816-6 data elements; data stored as ungrouped data elements encoded using ISO/IEC Abstract Syntax Notation (ASN.1) as in ISO/IEC 8824 and 8825; other proprietary techniques that may include fractal compression methods, image compression methods, etc.

In various embodiments, the ability to store a wide variety of information in different formats is facilitated by storing the information as a BLOB. Thus, any binary information can be stored in a storage space associated with a data set. As discussed above, the binary information may be stored in association with the system or external to but affiliated with the system. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data, in the database or associated with the system, by multiple and unrelated owners of the data sets. For example, a first data set which may be stored may be provided by a first party, a second data set which may be stored may be provided by an unrelated second party, and yet a third data set which may be stored may be provided by a third party unrelated to the first and second party. Each of these three exemplary data sets may contain different information that is stored using different data storage formats and/or techniques. Further, each data set may contain subsets of data that also may be distinct from other subsets.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The data may be big data that is processed by a distributed computing cluster. The distributed computing cluster may be, for example, a HADOOP® software cluster configured to process and store big data sets with some of nodes comprising a distributed storage system and some of nodes comprising a distributed processing system. In that regard, distributed computing cluster may be configured to support a HADOOP® software distributed file system (HDFS) as specified by the Apache Software Foundation at www.hadoop.apache.org/docs.

As used herein, the term "network" includes any cloud, cloud computing system, or electronic communications system or method which incorporates hardware and/or software components. Communication among the parties may be accomplished through any suitable communication channels, such as, for example, a telephone network, an extranet, an intranet, internet, point of interaction device (point of sale device, personal digital assistant (e.g., an IPHONE® device, a BLACKBERRY® device), cellular phone, kiosk, etc.), online communications, satellite communications, off-line communications, wireless communications, transponder communications, local area network (LAN), wide area network (WAN), virtual private network (VPN), networked or linked devices, keyboard, mouse, and/or any suitable communication or data input modality. Moreover, although the system is frequently described herein as being implemented with TCP/IP communications protocols, the system may also be implemented using IPX, APPLETALK® program, IP-6, NetBIOS, OSI, any tunneling protocol (e.g. IPsec, SSH, etc.), or any number of existing or future protocols. If the network is in the nature of a public network, such as the internet, it may be advantageous to presume the network to be insecure and open to eavesdroppers. Specific information related to the protocols, standards, and application software utilized in connection with the internet is generally known to those skilled in the art and, as such, need not be detailed herein.

Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand.

As used herein, "transmit" may include sending electronic data from one system component to another over a network connection. Additionally, as used herein, "data" may include encompassing information such as commands, queries, files, data for storage, and the like in digital or any other form.

Any communication, transmission, and/or channel discussed herein may include any system or method for delivering content (e.g. data, information, metadata, etc.), and/or the content itself. The content may be presented in any form or medium, and in various embodiments, the content may be delivered electronically and/or capable of being presented electronically. For example, a channel may comprise a website, mobile application, or device (e.g., FACEBOOK®, YOUTUBE®, PANDORA®, APPLE TV®, MICROSOFT® XBOX®, ROKU®, AMAZON FIRE®, GOOGLE CHROMECAST™, SONY® PLAYSTATION®, NINTENDO® SWITCH®, etc.) a uniform resource locator ("URL"), a document (e.g., a MICROSOFT® Word or EXCEL, an ADOBE® Portable Document Format (PDF) document, etc.), an "ebook," an "emagazine," an application or microapplication (as described herein), an short message service (SMS) or other type of text message, an email, a FACEBOOK® message, a TWITTER® tweet, multimedia messaging services (MMS), and/or other type of communication technology. In various embodiments, a channel may be hosted or provided by a data partner. In various embodiments, the distribution channel may comprise at least one of a merchant website, a social media website, affiliate or partner websites, an external vendor, a mobile device communication, social media network, and/or location based service. Distribution channels may include at least one of a merchant website, a social media site, affiliate or partner websites, an external vendor, and a mobile device communication. Examples of social media sites include FACEBOOK®, FOURSQUARE®, TWITTER®, LINKEDIN®, INSTAGRAM®, PINTEREST®, TUMBLR®, REDDIT®, SNAPCHAT®, WHATSAPP®, FLICKR®, VK®, QZONE®, WECHAT®, and the like. Examples of affiliate or partner websites include AMERICAN EXPRESS®, GROUPON®, LIVINGSOCIAL®, and the like. Moreover, examples of mobile device communications include texting, email, and mobile applications for smartphones.

The disclosure and claims do not describe only a particular outcome of a system for automated edit check generation, but the disclosure and claims include specific rules for implementing the outcome of a system for automated edit check generation and that render information into a specific format that is then used and applied to create the desired results of an automated edit check generation system, as set forth in *McRO, Inc. v. Bandai Namco Games America Inc.* (Fed. Cir. case number 15-1080, Sep. 13, 2016). In other words, the outcome of an automated edit check generation system can be performed by many different types of rules and combinations of rules, and this disclosure includes various embodiments with specific rules. While the absence of complete preemption may not guarantee that a claim is eligible, the disclosure does not sufficiently preempt the field of an automated edit check generation system at all. The disclosure acts to narrow, confine, and otherwise tie down the disclosure so as not to cover the general abstract idea of just an automated edit check generation system. Significantly, other systems and methods exist for automated edit check generation, so it would be inappropriate to assert that the claimed invention preempts the field or monopolizes the basic tools of an automated edit check generation system. In other words, the disclosure will not prevent others from an automated edit check generation system, because other systems are already performing the functionality in different ways than the claimed invention. Moreover, the claimed invention includes an inventive concept that may be found in the non-conventional and non-generic arrangement of known, conventional pieces, in conformance with *Bascom* v. *AT&T Mobility,* 2015-1763 (Fed. Cir. 2016). The disclosure and claims go way beyond any conventionality of any one of the systems in that the interaction and synergy of the systems leads to additional functionality that is not provided by any one of the systems operating independently. The disclosure and claims may also include the interaction between multiple different systems, so the disclosure cannot be considered an implementation of a generic computer, or just "apply it" to an abstract process. The disclosure and claims may also be directed to improvements to software with a specific implementation of a solution to a problem in the software arts.

What is claimed is:

1. A method, comprising:
   writing, by a computer based system, a template edit check based on a custom edit check, the template edit check comprising a parameter set;
   generating, by the computer based system, an edit check at least based on the template edit check and the parameter set; and
   determining, by the computer based system, a depth for each parameter of the parameter set, wherein the depth defines a number of elements in an array comprising one of a plurality of possible value types for a received parameter or a parsed parameter.

2. The method of claim 1, further comprising identifying, by the computer based system, the custom edit check prior to writing the template edit check.

3. The method of claim 1, further comprising, generating, by the computer based system, a dynamic code for each depth of the parameter set, wherein the dynamic code is configured to replace variables of the depth and generate the edit check.

4. The method of claim 3, wherein the dynamic code comprises:

```
For d=1
   block1 = block1 + "Loop a<d> where array.depth = <d>"
   block2 = block2 + "replace(text, prm(a<d>).name, prm(a<d>).value)"
   block3 = block3 + "end loop"
End loop
genCode = block1 + block2 +
"Loop x=1..Prm.len where type != 'ARRAY'"
+ "Replace (genEdit, Prm(x).name, Prm(x).value)"
+ "end loop"
+ "Save generated edit check"
``` wherein each of block1, block2, and block3 are a block of text, wherein genCode is a literal string comprising append text of block1, block2, block3 plus the addition code for non-array parameters, wherein the replace ( ) function replaces names with values, and wherein the prm ( ) is a function related to a parameter of the parameter set.

5. The method of claim 1, further comprising compiling, by the computer based system, rules data and a trial data to generate a study, wherein the rules data is associated with the trial data and the edit check.

6. A computer-based system, comprising:
   a processor; and
   a tangible, non-transitory memory configured to communicate with the processor, the tangible, non-transitory memory having instructions stored thereon that, in response to execution by the processor, cause the processor to perform operations comprising:
   writing, by a computer based system, a template edit check based on a custom edit check, the template edit check comprising a parameter set;
   generating, by the computer based system, an edit check at least based on the template edit check and the parameter set; and
   determining, by the computer based system, a depth for each parameter of the parameter set, wherein the depth defines a number of elements in an array comprising one of a plurality of possible value types for a received parameter or a parsed parameter.

7. The computer-based system of claim 6, wherein the operations further comprise identifying, by the computer based system, the custom edit check, wherein the identifying is performed prior to writing the template edit check.

8. The computer-based system of claim 6, wherein the operations further comprise generating, by the computer based system, a dynamic code for each depth of the parameter set, wherein the dynamic code is configured to replace variables of the depth and generate the edit check.

9. The computer-based system of claim 8, wherein the dynamic code comprises:

```
for d=1
   block1 = block1 + "Loop a<d> where array.depth = <d>"
   block2 = block2 + "replace(text, prm(a<d>).name, prm(a<d>).value)"
   block3 = block3 + "end loop"
End loop
genCode = block1 + block2 +
"Loop x=1..Prm.len where type != 'ARRAY'"
+ "Replace (genEdit, Prm(x).name, Prm(x).value)"
+ "end loop"
+ "Save generated edit check";
``` wherein each of block1, block2, and block3 are a block of text, wherein genCode is a literal string comprising append text of block1, block2, block3 plus the addition code for non-array parameters, wherein the replace ( ) function replaces names with values, and wherein the prm ( ) is a function related to a parameter of the parameter set.

10. The computer-based system of claim 6, wherein the operations further comprise compiling, by the computer based system, rules data and a trial data to generate a study, wherein the rules data is associated with the trial data and the edit check.

11. An article of manufacture including a non-transitory, tangible computer readable storage medium having instructions stored thereon that, in response to execution by a computer based system, cause the computer based system to perform operations comprising:
   generating, by a computer based system, an edit check at least based on a template edit check and a parameter set of the template edit check, the template edit check being based on a custom edit check; and determining, by the computer based system, a depth for each parameter of the parameter set, wherein the depth defines a number of elements in an array comprising one of a plurality of possible value types for a received parameter or a parsed parameter.

12. The article of manufacture of claim 11, wherein the operations further comprise identifying, by the computer based system, the custom edit check, wherein the identifying is performed prior to writing the template edit check.

13. The article of manufacture of claim 11, wherein the operations further comprise generating, by the computer based system, a dynamic code for each depth of the parameter set, wherein the dynamic code is configured to replace variables of the depth and generate the edit check.

14. The article of manufacture of claim 13, wherein the dynamic code comprises:

```
for d=1
  block1 = block1 + "Loop a<d> where array.depth = <d>"
  block2 = block2 + "replace(text, prm(a<d>).name, prm(a<d>).value)"
  block3 = block3 + "end loop"
End loop
genCode = block1 + block2 +
  "Loop x=1..Prm.len where type != 'ARRAY'"
  + "Replace (genEdit, Prm(x).name, Prm(x).value)"
  + "end loop"
  + "Save generated edit check";
``` wherein each of block1, block2, and block3 are a block of text, wherein genCode is a literal string comprising append text of block1, block2, block3 plus the addition code for non-array parameters, wherein the replace ( ) function replaces names with values, and wherein the prm ( ) is a function related to a parameter of the parameter set.

15. The article of manufacture of claim 11, wherein the operations further comprise compiling, by the computer based system, rules data and a trial data to generate a study, wherein the rules data is associated with the trial data and the edit check.

* * * * *